(12) United States Patent
Harvey

(10) Patent No.: US 6,547,194 B1
(45) Date of Patent: Apr. 15, 2003

(54) MAGNETIC THERAPEUTIC SUPPORT FOR AN UPPER EXTREMITY OF A USER USING AN ELECTRONIC COMPUTING DEVICE

(76) Inventor: John P. Harvey, 2084 Feuereisen Ave., Ronkonkoma, NY (US) 11779

( * ) Notice: Subject to any disclaimer, the term of this patent is extended or adjusted under 35 U.S.C. 154(b) by 0 days.

(21) Appl. No.: 09/838,375

(22) Filed: Apr. 19, 2001

(51) Int. Cl.⁷ ................................................. A61N 2/08
(52) U.S. Cl. ........................ 248/118; 248/918; 600/9; 600/15
(58) Field of Search ............................. 248/118, 118.1, 248/118.3, 118.5, 918; 600/9, 10, 11, 12, 13, 14, 15

(56) References Cited

U.S. PATENT DOCUMENTS

| | | | | |
|---|---|---|---|---|
| 4,330,892 A | * | 5/1982 | Fukushima | 5/421 |
| 5,131,614 A | * | 7/1992 | Garcia et al. | 248/118 |
| 5,183,230 A | * | 2/1993 | Walker et al. | 248/118 |
| 5,228,655 A | * | 7/1993 | Garcia et al. | 248/118 |
| 5,330,249 A | * | 7/1994 | Weber et al. | 2/161.1 |
| 5,562,270 A | * | 10/1996 | Montague | 248/118.1 |
| 5,642,739 A | * | 7/1997 | Fareed | 128/878 |
| 5,813,971 A | * | 9/1998 | Broderick | 600/15 |
| 5,817,000 A | | 10/1998 | Souder | 600/15 |
| 5,971,331 A | | 10/1999 | Getsay | 248/118 |
| 5,980,143 A | * | 11/1999 | Bayer et al. | 248/118.1 |
| 5,993,375 A | * | 11/1999 | Engel | 600/15 |
| 6,048,303 A | * | 4/2000 | Porter | 600/15 |
| 6,050,964 A | * | 4/2000 | Yates | 248/118 |
| 6,082,683 A | * | 7/2000 | Yates | 156/145 |
| 6,135,399 A | * | 10/2000 | Savoie et al. | 248/118 |
| 6,146,324 A | * | 11/2000 | Engel | 600/15 |
| 2001/0037047 A1 | * | 11/2001 | Mann | 600/15 |

* cited by examiner

Primary Examiner—Kimberly Wood
Assistant Examiner—Deborah M. Brann
(74) Attorney, Agent, or Firm—Richard L. Miller

(57) ABSTRACT

A magnetic support for an upper extremity of a user using an electronic computing device. The support includes a body, magnets attached to the body so as to form a first unit, and a covering that covers the first unit so as to form a second unit. In a first embodiment, the magnets extend upwardly from the body and the second unit extends along, and adjacent to, a keyboard when the electronic computing device is a keyboard. In a second embodiment, the second unit is integrally formed onto an end of a mouse pad when the electronic computing device is a mouse. In a third embodiment, the magnets depend into, and are flush with, the body and the second unit is a mouse pad when the electronic computing device is a mouse.

7 Claims, 1 Drawing Sheet

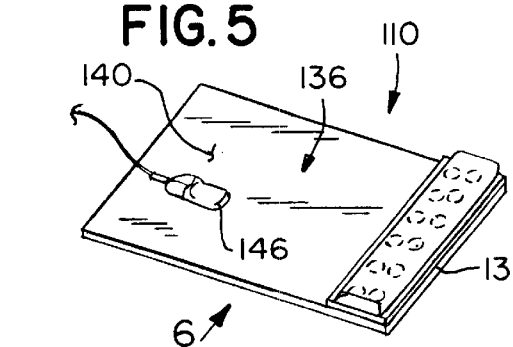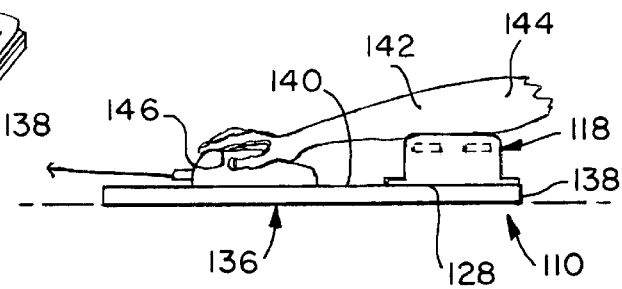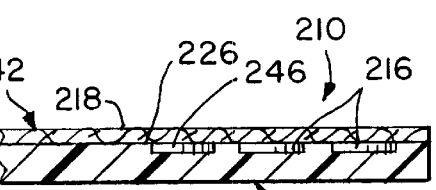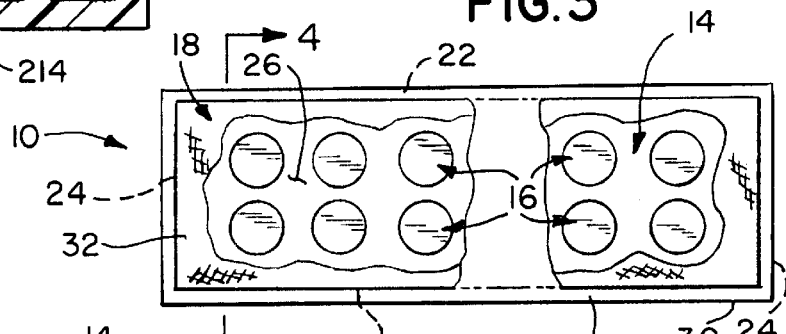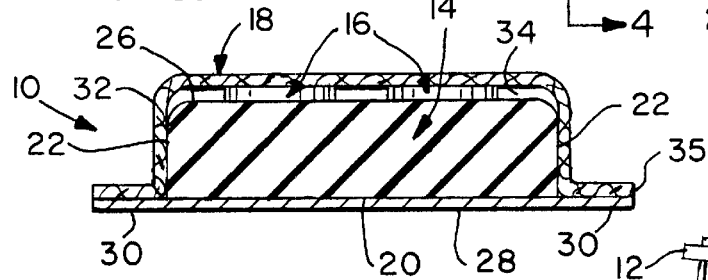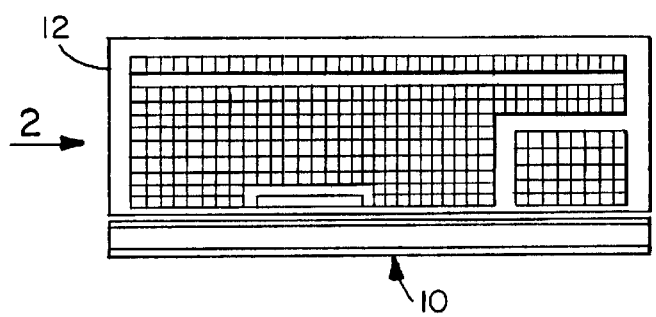

MAGNETIC THERAPEUTIC SUPPORT FOR AN UPPER EXTREMITY OF A USER USING AN ELECTRONIC COMPUTING DEVICE

BACKGROUND OF THE INVENTION

1. Field of the Invention

The present invention relates to a magnetic therapeutic support. More particularly, the present invention relates to a magnetic support for an upper extremity of a user using an electronic computing device.

2. Description of the Prior Art

Numerous innovations for therapy devices have been provided in the prior art, that will be described. Even though these innovations may be suitable for the specific individual purposes to which they address, however, they differ from the present invention.

A first example, U.S. Pat. No. 5,813,971 to Broderick teaches a housing comprising mutually engageable top and bottom parts which contain a lightweight ceramic plate magnet capable of producing a high field strength. A keeper plate is placed on top of the magnet overhanging its longitudinal edges so that blood flowing beneath the device successively encounters alternating north-south-north magnetic poles. The housing is secured to the body by a strap which is held between opposed lands.

A second example, U.S. Pat. No. 5,817,000 to Souder teaches the application of a moving magnetic field whereby a magnet moveable in a horizontal or vertical direction is placed proximate the user. The magnet is preferably contained within the interior cavity of a housing, the interior cavity being larger than the magnet, and the housing being positioned proximate to the user such that, as the magnet moves within the interior cavity of the housing, a moving magnetic field is generated which interacts with the surrounding tissue of the user. The housing may be attached to the user or to an object proximate to the user such that movements of the user or object cause the magnet within the interior cavity of the housing to move with respect to the user. Alternate embodiments include disposing the magnet on the end of a flexible handle or in an array.

A third example, U.S. Pat. No. 5,971,331 to Getsay teaches a wrist support for use with electronic computing devices that includes a plurality of rollers rotatably attached to roller supports, which are attached to a base. The rollers are positioned arcuately within the roller supports having a center roller positioned at a slightly higher elevation as compared to adjacent rollers. The rollers have protuberances at each end for engagement with holes in the roller supports for enabling the rollers to rotate about an axis. The rollers may also be inclined at a first angle extending from an inner roller support toward an end roller support and at a second angle extending from the inner roller support toward the other end roller support. Pads are attached to the base for enabling the base to flex and provide a cushion between the base and a support surface. Spacers are attached to the base so that the rollers contact the spacers instead of contacting the base. The wrist support may additionally include a pivot attached to the base and to support for enabling the base and rollers to pivot about the support for use with a computer mouse. Alternatively, the wrist support may include an expandable member attached to a two piece base for enabling a person to adjust the space between adjacent sets of rollers.

A fourth example, U.S. Pat. No. 6,048,303 to Porter teaches apparatus for applying magnetic flux to tissue utilizing strip-shaped flexible polymeric permanent magnets. The magnets are reinforced with an adhesively applied tape and removably inserted into retainer pockets or channels formed within a support structure. In one embodiment, the support structure is formed of two flexible mat components which are sewn together to form the retention pockets. A wrist rest embodiment utilizes a thin flexible platform to support the magnetic components within retention channels in combination with a foamaceous support structure.

A fifth example, U.S. Pat. No. 6,135,399 to Savoie et al. teaches a forearm, wrist and hand support apparatus, with rotatable rollers, for operators of, and to be used with computer keyboards, calculators, computer mice and other equipment requiring repetitive hand operation. The apparatus (relaxer) is comprised of two sets of round, rotatable rollers for equipment requiring two hand-operation, and one set of round, rotatable rollers for equipment requiring one-hand operation. The operator can rest his/her hand(s) while pausing during the input process, and need only move his/her wrist(s) and hand(s) on the round (cylindrical) rollers during the input process thus creating a massaging action. The use of the wrist relaxer will help maintain the operator's shoulder(s), arm(s), wrist(s) and hand(s) in a healthy condition.

It is apparent that numerous innovations for therapy devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

Accordingly, an object of the present invention is to provide a magnetic support for an upper extremity of a user using an electronic computing device that avoids the disadvantages of the prior art.

Another object of the present invention is to provide a magnetic support for an upper extremity of a user using an electronic computing device that is simple and inexpensive to manufacture.

Still another object of the present invention is to provide a magnetic support for an upper extremity of a user using an electronic computing device that is simple to use.

Briefly stated, still yet another object of the present invention is to provide a magnetic support for an upper extremity of a user using an electronic computing device. The support includes a body, magnets attached to the body so as to form a first unit, and a covering that covers the first unit so as to form a second unit. In a first embodiment, the magnets extend upwardly from the body and the second unit extends along, and adjacent to, a keyboard when the electronic computing device is a keyboard. In a second embodiment, the second unit is integrally formed onto an end of a mouse pad when the electronic computing device is a mouse. In a third embodiment, the magnets depend into, and are flush with, the body and the second unit is a mouse pad when the electronic computing device is a mouse.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows:

FIG. 1 is a diagrammatic top plan view of a first embodiment of the present invention in use;

FIG. 2 is a diagrammatic side elevational view taken generally in the direction of arrow 2 in FIG. 1;

FIG. 3 is an enlarged diagrammatic top plan view taken generally in the direction of arrow 3 in FIG. 2;

FIG. 4 is an enlarged diagrammatic cross sectional view taken on line 4—4 in FIG. 3;

FIG. 5 is a diagrammatic perspective view of a second embodiment of the present invention in use;

FIG. 6 is a diagrammatic side elevational view taken generally in the direction of arrow 6 in FIG. 5; and FIG. 7 is a diagrammatic cross sectional view of a third embodiment of the present invention.

LIST OF REFERENCE NUMERALS UTILIZED IN THE DRAWING

First Embodiment 10 magnetic support of present invention for upper extremity of user using keyboard 12
12 keyboard
14 body for extending along, and adjacent to, keyboard 12
16 magnets
18 covering
20 lowermost surface of body 14
22 pair of long sides of body 14
24 pair of short sides of body 14
26 uppermost surface of body 14
28 bottom portion of covering 18
30 lower peripheral lip completely around bottom portion 28 of covering 18
32 top portion of covering 18
34 air space formed between top portion 32 of covering 18 and uppermost surface 26 of body 14 for conveying, so as not to inhibit, magnetic fields of magnets 16.
35 upper peripheral lip terminating top portion 32 of covering 18 and extending completely therearound

Second Embodiment 110 magnetic support
136 mouse pad
138 periphery of mouse pad 136
140 uppermost surface of mouse pad 136

Third Embodiment 210 magnetic support
214 body
216 magnets
218 covering
226 uppermost surface of body 214
242 mouse pad
246 top surfaces of magnets 216

DETAILED DESCRIPTION OF THE PREFERRED EMBODIMENT

Referring now to the figures, in which like numerals indicate like parts, and particularly to FIGS. 1 and 2, a first embodiment of the magnetic support of the present invention is shown generally at 10 for an upper extremity of a user using a keyboard 12.

The configuration of the magnetic support 10 can best be seen in FIGS. 3 and 4, and as such, will be discussed with reference thereto.

The magnetic support 10 comprises a body 14, magnets 16 that are attached to the body 14 so as to form a first unit, and a covering 18 that covers the first unit so as to form a second unit.

The body 14 is a rectangular-parallelepiped-shaped pad for extending along, and adjacent to, the keyboard 12.

The body 14 has a lowermost surface 20 that is flat, a pair of long sides 22 that are flat and extend upwardly from the lowermost surface 20 thereof, with one long side 22 thereof for extending along, and adjacent to, the keyboard 12, in its entirety, a pair of short sides 24 that are shorter than the pair of long sides 22 thereof, respectively, and which extend upwardly from the lowermost surface 20 thereof, and an uppermost surface 26 that is flat and disposed above the lowermost surface 20 thereof.

The magnets 16 are disk-shaped.

The magnets 16 are attached to, and extend upwardly a short distance from but not in, the uppermost surface 26 of the body 14.

The magnets 16 are equally spaced-apart from each other in two equally spaced-apart rows on the uppermost surface 26 of the body 14 for allowing the magnetic fields of adjacent ones of the magnets 16 to overlap each other and cover the uppermost surface 26 of the body 14, in its entirety, so as to allow the magnetic fields to be available for the upper extremity of the user regardless of where the upper extremity of the user is placed on the uppermost surface 26 of the body 14.

The covering 18 is a fabric sheet.

The covering 18 comprises a bottom portion 28 that directly underlies the lowermost surface 20 of the body 14, in its entirety.

The bottom portion 28 of the covering 18 extends slightly past both the pair of long sides 22 of the body 14 and the pair of short sides 24 of the body 14 so as to form a lower peripheral lip 30 completely therearound.

The covering 18 further comprises a top portion 32 that directly overlies the pair of long sides 22 of the body 14, in their entirety, and the pair of short sides 24 of the body 14, in their entirety, while directly overlying the magnets 16, and forming an air space 34 with the uppermost surface 26 of the body 14, by virtue of the magnets 16 extending a short distance upwardly from the uppermost surface 26 of the body 14, for conveying, so as not to inhibit, the magnetic fields of the magnets 16.

The top portion 32 of the covering 18 terminates in an upper peripheral lip 35 that extends completely therearound and which attaches to the lower peripheral lip 30, and together therewith, encases the first unit in the covering 18, in its entirety.

A second embodiment of the magnetic support 110 can best be seen in FIGS. 5 and 6, and as such, will be discussed with reference thereto.

The magnetic support 110 is similar to the magnetic support 10, except for the addition of a mouse pad 136 that is integral attached thereto.

The mouse pad 136 has a periphery 138 and an uppermost surface 140.

The second unit is integrally formed to the uppermost surface 140 of the mouse pad 136 and extends along an end of the periphery 138 of the mouse pad 136 that is suitable for supporting an upper extremity 142 of a user 144 when the electronic computing device 12 is a mouse.

A third embodiment of the magnetic support 210 can best be seen in FIG. 7, and as such, will be discussed with reference thereto.

The magnetic support 210 is similar to the magnetic support 10, except that the magnetic support 210 is a mouse pad 242.

The body 214 is a flat pad.

The magnets 216 depend into, and remain flush with, the uppermost surface 226 of the body 214 so as to have exposed only top surfaces 246, and are disposed at one end of the body 214.

The covering 218 directly overlies only the uppermost surface 226 of the body 214, in its entirety, and the top surfaces 246 of the magnets 216, in their entireties.

It will be understood that each of the elements described above, or two or more together, may also find a useful application in other types of constructions differing from the types described above.

While the invention has been illustrated and described as embodied in a magnetic wrist support for use with electronic computing devices, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A magnetic support for an upper extremity of a user using an electronic computing device, comprising:
    a) a body;
    b) magnets attached to said body so as to form a first unit; and
    c) a covering covering said first unit so as to form a second unit;
    wherein said body is a rectangular-parallelepiped-shaped pad for extending along, and adjacent to, a keyboard when the electronic computing device is a keyboard;
    wherein said body has:
        i) a lowermost surface that is flat;
        ii) a pair of long sides that are flat and extend upwardly from said lowermost surface thereof, with one long side thereof for extending along, and adjacent to, the keyboard, in its entirety when the electronic computing device is the keyboard;
        iii) a pair of short sides that are shorter than said pair of long sides thereof, respectively, and which extend upwardly from said lowermost surface thereof; and
        iv) an uppermost surface that is flat and disposed above said lowermost surface thereof;
    wherein said magnets are equally spaced-apart from each other in two equally spaced-apart rows on said uppermost surface of said body for allowing the magnetic fields of adjacent ones of said magnets to overlap each other and cover said uppermost surface of said body, in its entirety, so as to allow said magnetic fields to be available for the upper extremity of the user regardless of where the upper extremity of the user is placed on said uppermost surface of said body;
    wherein said covering comprises:
        i) a bottom portion that directly underlies said lowermost surface of said body, in its entirety; wherein said bottom portion of said covering extends slightly past both said pair of long sides of said body and said pair of short sides of said body so as to form a lower peripheral lip completely therearound; and
        ii) a top portion that directly overlies said pair of long sides of said body, in their entirety, and said pair of short sides of said body, in their entirety, while directly overlying said magnets, and forming an air space with said uppermost surface of said body around each magnet that communicate with each other so as to form a continuous air space, by virtue of said magnets extending a short distance upwardly from said uppermost surface of said body, for conveying, so as not to inhibit the magnetic fields of adjacent ones of said magnets from overlapping each other and covering said uppermost surface of said body, in its entirety, wherein the top portion of said covering is a fabric sheet.

2. The support as defined in claim 1, wherein said magnets are disk-shaped.

3. The support as defined in claim 1, wherein said magnets are attached to, and extend upwardly a short distance from, said uppermost surface of said body.

4. The support as defined in claim 1, wherein said top portion of said covering terminates in an upper peripheral lip that extends completely therearound and which attaches to said lower peripheral lip, and together therewith, encases said first unit in said covering, in its entirety.

5. The support as defined in claim 1; further comprising a mouse pad integrally attached to said second unit.

6. The support as defined in claim 5, wherein said mouse pad has:
    a) a periphery; and
    b) an uppermost surface.

7. The support as defined in claim 6, wherein said second unit is integrally formed to said uppermost surface of said mouse pad and extends along an end of said periphery of said mouse pad that is suitable for supporting the upper extremity of the user when the electronic computing device is a mouse.

* * * * *